(12) United States Patent
Zhou et al.

(10) Patent No.: US 11,857,644 B2
(45) Date of Patent: Jan. 2, 2024

(54) MULTI-SIGNAL FLUORESCENT PROBE FOR EARLY DIAGNOSIS OF TUMORS, AND PREPARATION AND USE THEREOF

(71) Applicants: Hunan Cancer Hospital, Changsha (CN); Hunan Normal University, Changsha (CN)

(72) Inventors: Huijun Zhou, Changsha (CN); Zhenyang Liu, Changsha (CN); Pan Chen, Changsha (CN); Xiaming Zhang, Changsha (CN); Peng Yin, Changsha (CN); Ting Li, Changsha (CN)

(73) Assignees: Hunan Cancer Hospital, Changsha (CN); Hunan Normal University, Changsha (CN)

( * ) Notice: Subject to any disclaimer, the term of this patent is extended or adjusted under 35 U.S.C. 154(b) by 53 days.

(21) Appl. No.: 18/189,238

(22) Filed: Mar. 24, 2023

(65) Prior Publication Data
US 2023/0226226 A1    Jul. 20, 2023

(30) Foreign Application Priority Data
Apr. 25, 2022    (CN) .......................... 202210441449.6

(51) Int. Cl.
*A61B 5/00* (2006.01)
*A61B 8/00* (2006.01)
*A61B 10/00* (2006.01)
*A61K 49/00* (2006.01)

(52) U.S. Cl.
CPC ................................. *A61K 49/003* (2013.01)

(58) Field of Classification Search
None
See application file for complete search history.

(56) References Cited

FOREIGN PATENT DOCUMENTS

| CN | 113135948 A | 7/2021 |
|---|---|---|
| CN | 114163456 A | 3/2022 |
| CN | 114249760 A | 3/2022 |

OTHER PUBLICATIONS

Jiaojiao Liu et al., "A phenothiazine coumarin based ratiometric fluorescent probe for real-time detection of lysosomal hypochlorite in living cell and zebra fish", Spectrochimica Acta Part A: Molecular and Biomolecular Spectroscopy 261 (2021) 120024.

Jiali Chen et al., "De Novo Design of a Robust Fluorescent Probe for Basal HClO Imaging in a Mouse Parkinson's Disease Model", ACS Chem. Neurosci. 2021, 12, pp. 4058-4064.

Ashutosh Barve et al., "Synthesis and antimicrobial activity of novel oxime derivatives of phenothiazine", European Journal of Chemistry 2 (3) (2011), pp. 388-393.

Tonghui Huang et al., "Dual-Responsive Ratiometric Fluorescent Probe for Hypochlorite and Peroxynitrite Detection and Imaging In Vitro and In Vivo", Analytical Chemistry, 2022, 94, 2, pp. 1415-1424.

*Primary Examiner* — Michael G. Hartley
*Assistant Examiner* — Melissa J Perreira

(57) ABSTRACT

A multi-signal fluorescent probe, represented by:

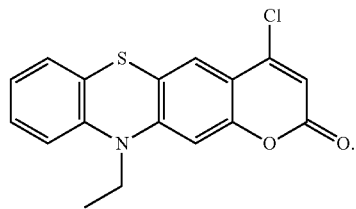

A method for preparing the multi-signal fluorescent probe includes: (a) adding 2-methoxyphenothiazine and ethyl iodide into a mixture of dichloromethane (DCM) and acetonitrile followed by a first reaction and a first post-treatment to obtain 10-ethyl-2-methoxy-10H-phenothiazine; (b) adding boron tribromide into the 10-ethyl-2-methoxy-10H-phenothiazine under an inert gas followed by a second reaction under an ice bath and a second post-treatment to obtain 10-ethyl-10H-phenothiazin-2-ol; and (c) mixing the 10-ethyl-10H-phenothiazin-2-ol, malonic acid, zinc chloride and phosphorus oxychloride followed by a third reaction and a third post-treatment to obtain the multi-signal fluorescent probe. A use of the multi-signal fluorescent probe in the detection of intracellular $ONOO^-$ and $Na_2S_2$ is also provided.

10 Claims, 1 Drawing Sheet

MULTI-SIGNAL FLUORESCENT PROBE FOR EARLY DIAGNOSIS OF TUMORS, AND PREPARATION AND USE THEREOF

CROSS-REFERENCE TO RELATED APPLICATIONS

This application claims the benefit of priority from Chinese Patent Application No. 202210441449.6, filed on Apr. 25, 2022. The content of the aforementioned application, including any intervening amendments thereto, is incorporated herein by reference in its entirety.

TECHNICAL FIELD

The present application relates to analytical chemistry, and more particularly to a multi-signal fluorescent probe for early diagnosis of tumors, and a preparation and use thereof.

BACKGROUND

Reactive oxygen species (ROS) and reactive nitrogen species (RNS) play important roles in regulating various physiological functions, and are involved in various pathophysiological processes, such as cancer, aging, signal transduction, cellular redox homeostasis and defense against pathogen invasion. Peroxynitrite ($ONOO^-$), a common type of RNS, plays an essential role in various physiological and pathological processes. It has been evidenced that excess $ONOO^-$ is associated with various human diseases, such as hypertension, gastric cancer, neurodegenerative diseases, and inflammatory diseases. In addition, sodium disulfide ($Na_2S_2$) plays an important role in regulating the intracellular redox status and basic signal transduction. Accordingly, it is of great significance for the early diagnosis of related diseases to develop an efficient method or technique for simultaneous discrimination and detection of $ONOO^-$ and $Na_2S_2$.

Due to characteristics of real-time detection, high sensitivity and non-invasion, the small-molecule fluorescent probe-based fluorescence imaging technology has become an effective strategy for visualizing the spatio-temporal distribution of biomolecules in biological samples. At present, many small-molecule fluorescent probes have been developed for the detection of $ONOO^-$, and some single- or double-channel fluorescent probes have been emerged as an effective tool for the detection of $ONOO^-/Na_2S_2$.

Unfortunately, the existing fluorescent probes fail to enable the simultaneous discrimination and detection of $ONOO^-$ and $Na_2S_2$, and thus cannot be applied to the dual-channel ratiometric fluorescence imaging analysis of endogenous $ONOO^-$ and $Na_2S_2$.

SUMMARY

In order to overcome the problems in the prior art, the present disclosure provides a multi-signal fluorescent probe for early diagnosis of tumors, and a preparation and use thereof.

Technical solutions of this application are described as follows.

In a first aspect, the present disclosure provides a multi-signal fluorescent probe for early diagnosis of tumors, wherein a structural formula of the multi-signal fluorescent probe is shown as follows:

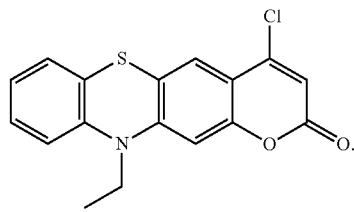 [SMILES: CCN1c2ccccc2Sc2cc3c(Cl)cc(=O)oc3cc21]

In a second aspect, the present disclosure provides a method for preparing the multi-signal fluorescent probe, comprising:

adding 2-methoxyphenothiazine and ethyl iodide into a mixture of dichloromethane (DCM) and acetonitrile followed by a first reaction to obtain a reaction mixture; and subjecting the reaction mixture to a first post-treatment to obtain 10-ethyl-2-methoxy-10H-phenothiazine;

adding boron tribromide into the 10-ethyl-2-methoxy-10H-phenothiazine under an inert gas followed by a second reaction under an ice bath and a second post-treatment to obtain 10-ethyl-10H-phenothiazin-2-ol; and mixing the 10-ethyl-10H-phenothiazin-2-ol, malonic acid, zinc chloride and phosphorus oxychloride followed by a third reaction and a third post-treatment to obtain the multi-signal fluorescent probe.

In some embodiments, the first reaction is performed at 65-75° C. for 8-12 h.

In some embodiments, the first post-treatment comprises:
subjecting the reaction mixture to column chromatography to obtain the 10-ethyl-2-methoxy-10H-phenothiazine.

In some embodiments, the second reaction is performed under stirring in a dark environment for 4-6 h.

In some embodiments, the second post-treatment comprises:
dropwise adding a red reaction solution resulted from the second reaction into ice water followed by pH adjustment to 6-7 and extraction with DCM to collect an organic layer; and concentrating the organic layer to obtain the 10-ethyl-10H-phenothiazin-2-ol.

In some embodiments, the third reaction is performed under reflux and stirring at 80-90° C. for 24-36 h.

In some embodiments, the third post-treatment comprises:
dropwise adding a brown viscous solution resulted from the third reaction into ice water followed by pH adjustment to 6-7 and extraction with DCM to collect an organic layer; and
subjecting the organic layer to concentration and column chromatography to obtain the multi-signal fluorescent probe.

In some embodiments, the pH adjustment is performed with a 20% sodium hydroxide aqueous solution.

In a third aspect, the present disclosure provides a method for detecting $ONOO^-$ and $Na_2S_2$ in cells, comprising:
detecting $ONOO^-$ and $Na_2S_2$ in the cells by using the multi-signal fluorescent probe.

Compared to the prior art, this application has the following beneficial effects.

The multi-signal fluorescent probe provided herein itself emits 610 nm red light under 410 nm excitation wavelength. After reacted with $ONOO^-$, it can emit 492 nm green light under 380 nm excitation wavelength; and after reacted with $Na_2S_2$, it can emit 548 nm yellow light under 410 nm excitation wavelength. The multi-signal fluorescent probe itself emits red fluorescence, and can undergo different reactions respectively with $ONOO^-$ and $Na_2S_2$ under the same detection condition to generate different fluorescent matters, so as to emit green and yellow fluorescence under the specific excitation wavelengths. Therefore, multi-signal fluorescent probe provided herein enables the simultaneous ratiometric discrimination and detection of ONOO⁻ and $Na_2S_2$, and thus can be applied in the analytical detection and early medical diagnosis.

BRIEF DESCRIPTION OF THE DRAWINGS

In order to explain the technical solutions of the present disclosure more clearly, the accompanying drawings needed in the description of the embodiments of the present disclosure will be briefly described below. Obviously, presented in the accompany drawings are merely some embodiments of the present disclosure, which are not intended to limit the disclosure.

DETAILED DESCRIPTION OF EMBODIMENTS

Figure 1:
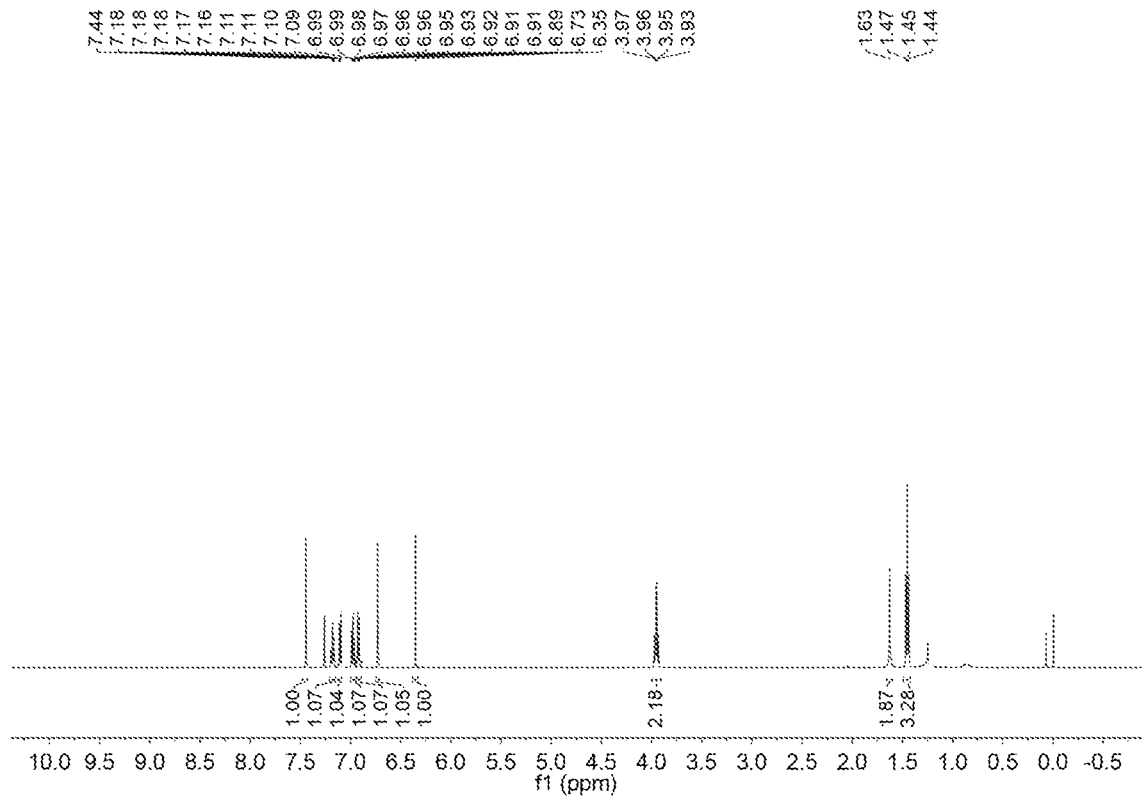
FIG. 1 shows a proton nuclear magnetic resonance ($^1$H-NMR) spectrum of a multi-signal fluorescent probe according to an embodiment of the present disclosure.

It should be noted that "prepared by . . . " is synonymous with "include". In addition, the term "include", "have", "contain" or any other variant thereof is intended to cover non-exclusive inclusion. For example, a process, method, article, or apparatus/device need not be limited to those listed elements, but may include other elements that are not explicitly listed or inherent to the process, method, article or device. The term "consist of" excludes any unspecified elements or components. This term has a closed meaning when used in claims, indicating the exclusion of other unspecified materials except for conventional impurities associated therewith. When the phrase "consist of" appears in a clause in the body of a claim rather than immediately following the subject matter, it is only to limit the element described in such clause; other elements are not excluded from the claim as a whole.

When amount, concentration, or other value or parameter is expressed as a range, a preferred range, or a range defined by a series of upper preferred values and lower preferred values, it should be understood as specifically disclosing all ranges formed by any pairing of any upper limit or preferred value with any lower limit or preferred value, regardless of whether such range is separately disclosed. For example, a range "1-5" should be interpreted to include ranges of "1-4", "1-3", "1-2", "1-2 and 4-5", and "1-3 and 5". Unless otherwise indicated, the numerical range described herein is intended to include its endpoints and all integers and fractions within the range.

In this application, the parts and percentages are expressed by weight unless otherwise indicated.

The phrase "part by weight" refers to a basic measurement unit indicating the mass ratio relationship of multiple components. For example, 1 part can represent any unit of mass, such as 1 g and 2.689 g. If it is specified that there are a parts by weight of component A and b parts by weight of component B, it means a mass ratio of A to B is a:b, or indicates that the mass of component A is aK and the mass of component B is bK (K is an arbitrary value, representing a multiplication factor). It should be noted that the sum of the parts by weight of all the components is not limited to 100 parts.

The term "and/or" indicates that one or both of the specified conditions may occur, for example, "A and/or B" includes "A", "B", and "a combination of A and B".

Provided is a multi-signal fluorescent probe for early diagnosis of a tumor, where structural formula of the multi-signal fluorescent probe is shown as follows:

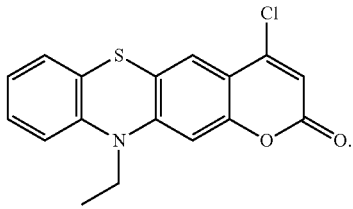 [SMILES: CCN1c2ccccc2Sc2cc3c(Cl)cc(=O)oc3cc21]

A method for preparing the multi-signal fluorescent probe is also provided, including:

adding 2-methoxyphenothiazine and ethyl iodide into a mixture of DCM and acetonitrile followed by a first reaction to obtain a reaction mixture; and subjecting the reaction mixture to a first post-treatment to obtain 10-ethyl-2-methoxy-10H-phenothiazine;

adding boron tribromide into the 10-ethyl-2-methoxy-10H-phenothiazine under an inert gas, followed by a second reaction under an ice bath and a second post-treatment to obtain 10-ethyl-10H-phenothiazin-2-ol; and mixing the 10-ethyl-10H-phenothiazin-2-ol, malonic acid, zinc chloride and phosphorus oxychloride followed by a third reaction and a third post-treatment to obtain the multi-signal fluorescent probe.

In an embodiment, the first reaction is performed at 65-75° C. for 8-12 h.

In an embodiment, the first reaction is performed at 65° C., 70° C., 75° C. or any temperature between 65-75° C. for 8 h, 10 h, 12 h or any duration between 8-12 h.

In an embodiment, the first post-treatment includes:

subjecting the reaction mixture to column chromatography to obtain the 10-ethyl-2-methoxy-10H-phenothiazine.

In an embodiment, the second reaction is performed under stirring in a dark environment for 4-6 h.

In an embodiment, the second post-treatment includes:

dropwise adding a red solution resulted from the second reaction into ice water followed by pH adjustment to 6-7 and extraction with DCM to collect an organic layer; and concentrating the organic layer to obtain the 10-ethyl-10H-phenothiazin-2-ol.

In an embodiment, the third reaction is performed under reflux and stirring at 80-90° C. for 24-36 h.

In an embodiment, the third reaction is performed at 80° C., 85° C., 90° C. or any temperature within 80-90° C. for 24 h, 30 h, 36 h or any duration within 24-36 h.

In an embodiment, the third post-treatment includes:

dropwise adding a brown viscous solution resulted from the third reaction into ice water followed by pH adjustment to 6-7 and extraction with DCM to collect an organic layer; and subjecting the organic layer to concentration and column chromatography to obtain the multi-signal fluorescent probe.

In an embodiment, the pH adjustment is performed with a 20 wt. % sodium hydroxide aqueous solution.

The present disclosure also provides a use of the multi-signal fluorescent probe in the detection of ONOO⁻ and $Na_2S_2$ in cells.

The present disclosure will be described in detail below with reference to the embodiments. Obviously, described below are merely some embodiments of this disclosure, and are not intended to limit the disclosure. Unless otherwise specified, the materials and reagents used in the following embodiments are available commercially, and the experiments are carried out using conventional methods.

A synthesis route of the multi-signal fluorescent probe is illustrated as follows:

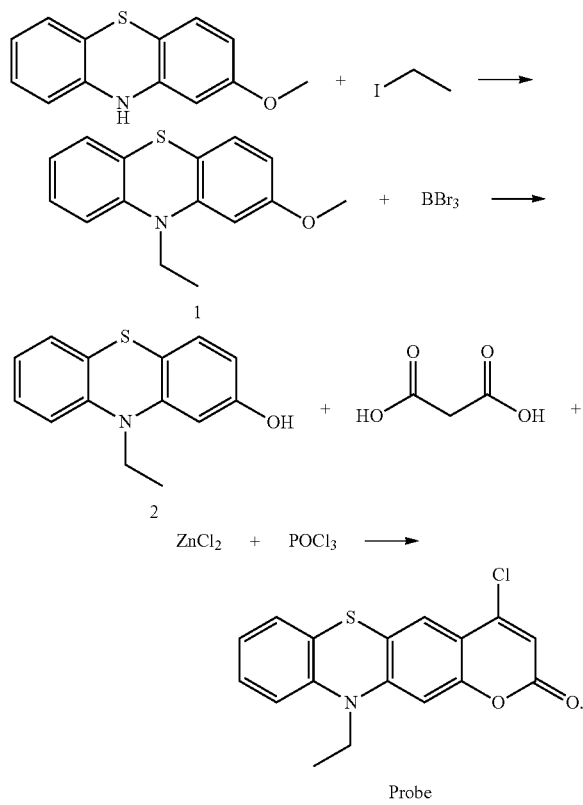

EXAMPLE (S1) Synthesis of 10-ethyl-2-methoxy-10H-phenothiazine (1a) 2.0 g (8.72 mmol) of 2-methoxyphenothiazine and 3.26 g (20.93 mmol) of ethyl iodide were added into 20 mL of DCM-acetonitrile mixture. The reaction mixture was reacted at 65° C. for 8-12 h.

(1b) After cooled to room temperature, the reaction mixture was subjected to column chromatography to obtain 616 mg of white solid as 10-ethyl-2-methoxy-10H-phenothiazine (yield: 27.5%).

(S2) Synthesis of 10-ethyl-10H-phenothiazin-2-ol (2a) 5.84 g (23.31 mmol) of boron tribromide ($BBr_3$) was slowly added into a solution of the 10-ethyl-2-methoxy-10H-phenothiazine (1.0 g, 3.89 mmol) in DCM under the protection of nitrogen gas. The reaction mixture was stirred on an ice bath in the dark for 4-6 h to obtain a red solution.

(2b) The red solution was slowly dropwise added into ice water, and the resultant mixture was adjusted to pH 6-7 with a 20 wt. % sodium hydroxide aqueous solution.

(2c) The reaction mixture was subjected to multiple extractions with DCM, and the resultant organic layers were collected, combined and subjected to rotary evaporation to obtain 600 mg of a light green solid as 10-ethyl-10H-phenothiazin-2-ol (yield: 63.46%).

(S3) Synthesis of 4-chloro-11-ethylpyrano[2,3-b]phenothiazin-2(11H)-one (the multi-signal fluorescent probe)

(3a) The 10-ethyl-10H-phenothiazin-2-ol, malonic acid and zinc chloride were mixed in a phosphorus oxychloride solution, and reacted under stirring and air reflux at 80° C. for 24 h to obtain a brown viscous solution.

(3b) The brown viscous solution was slowly dropwise added into ice water, and the resultant mixture was adjusted to pH 6-7 with a 20 wt. % sodium hydroxide aqueous solution.

(3c) The reaction mixture was subjected to multiple extractions with DCM, and the resultant organic layers were collected, combined, and subjected to rotary evaporation and column chromatography to obtain a yellow solid as 4-chloro-11-ethylpyrano[2,3-b]phenothiazin-2(11H)-one (yield: 30.3%)

The $^1$H-NMR spectrum of the multi-signal fluorescent probe was shown in FIG. 1.

The multi-signal fluorescent probe synthesized herein was capable of distinguishing and detecting $ONOO^-$ and $Na_2S_2$ produced in organisms. Unless otherwise specified, the experimental procedures were similar to those of other probes.

Spectral properties of the multi-signal fluorescent probe were investigated as follows.

The multi-signal fluorescent probe was dissolved with dimethyl sulfoxide (DMSO) to obtain a 1 mM probe solution. A 1 mM $ONOO^-$ aqueous solution and a 1 mM $Na_2S_2$ aqueous solution were prepared.

20 μL of the 1 mM probe solution, 980 μL of analytically pure $CH_3CN$, the required amount of the 1 mM $ONOO^-$ or $Na_2S_2$ aqueous solution and the required amount of phosphate buffered saline (PBS) were added into a 2 mL sample tube. A volume ratio of an organic phase to an aqueous phase was kept at 5:5 for all tests (a total volume of each test sample was 2 mL).

For example, when it was required to explore the fluorescence intensity of the multi-signal fluorescent probe after reacted with 20 mM $ONOO^-$, the experiment was formulated as follows.

Figure 2:
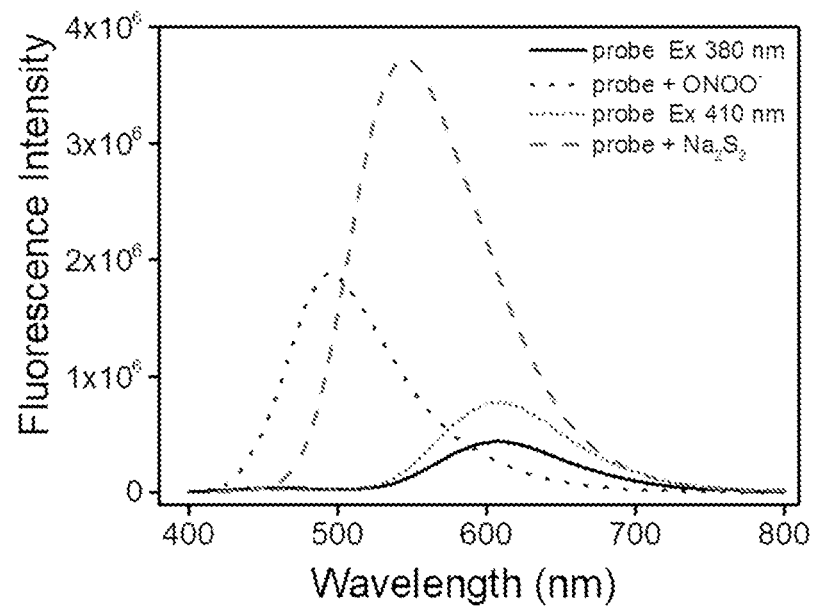
FIG. 2 shows a fluorescence spectrum of the multi-signal fluorescent probe according to an embodiment of the present disclosure in the presence of peroxynitrite and sodium disulfide.

L of the 1 mM probe solution, 980 μL of analytically pure $CH_3CN$, 20 μL of the 1 mM $ONOO^-$ aqueous solution and 980 μL of PBS were added into a 2 mL sample tube. The reaction mixture was mixed evenly under shaking at room temperature for 15 min. Then, the fluorescence emission intensity of the reaction mixture could be measured under the 350 nm excitation wavelength. Other steps were performed as above. The limit of detection (LOD) for $ONOO^-$ was 42.12 nM, and the LOD for $Na_2S_2$ was 38.45 nM. Fluorescence spectra of the multi-signal fluorescent probe in the detection of peroxynitrite and sodium disulfide were shown in FIG. 2. Accordingly, the highly-sensitive discrimination and detection for $ONOO^-$ and $Na_2S_2$ were realized by using the multi-signal fluorescent probe provided herein.

The multi-signal fluorescent probe provided herein is efficient and simple for the detection of oxidative and reductive substances, and can be used to discriminate and detect $ONOO^-$ and $Na_2S_2$ simultaneously. The multi-signal fluorescent probe can undergo different reactions respectively with $ONOO^-$ and $Na_2S_2$ under the same condition to generate different fluorescent matters which will emit green fluorescence and yellow fluorescence under specific wavelength. Therefore, $ONOO^-$ and $Na_2S_2$ can be simultaneously distinguished and detected, and the simultaneous dual-channel fluorescence imaging of endogenous $ONOO^-$ and $Na_2S_2$ in cells can be realized, which will facilitate the development of multi-signal bio-fluorescent probes.

The multi-signal fluorescent probe provided herein utilizes a dual-channel fluorescent signal to discriminate and detect ONOO⁻ and $Na_2S_2$ simultaneously, developing the fields of analysis and detection and medical early diagnosis.

Regarding a method for detecting ONOO⁻ and $Na_2S_2$ in cells, unless otherwise specified, a probe molecule is dissolved at room temperature for analytical detection, where a volume ratio of an organic phase to an aqueous phase is 5:5. The organic phase is acetonitrile ($CH_3CN$), and the aqueous phase is formed by PBS (pH=7.4) and an aqueous solution of the analyte.

The multi-signal fluorescent probe for reactive oxygen was dissolved in a solution, in which a volume ratio of DMSO to the aqueous phase was 5:5. The multi-signal fluorescent probe emitted 492 nm green light under 380 nm excitation wavelength after reacted with ONOO⁻, and emitted 548 nm yellow light under 410 nm excitation wavelength after reacted with $Na_2S_2$. Accordingly, a specific analyte can be detected by the specific excitation and fluorescence emission signal. The ONOO⁻ and $Na_2S_2$ can be distinguished by using different excitation wavelengths and fluorescence emission signals. The multi-signal fluorescent probe can detect the ONOO⁻ and $Na_2S_2$ simultaneously, and has no significant response to amino acids, sulfur-containing derivatives and amine derivatives, such as OH, t-BuO, $^1O_2$, NO, $O_2^-$, GSH, Cys, Hcy, $SO_2$, NAC, $H_2S$, F-, Cl-, Br⁻, I⁻, NAC, Gly, Ala, His, Met, Thr, Lys, Asp, Glu, Pro, Ser, NaHS, $NaHSO_3$, EtSH, PhSH, n-Butylamine, and aniline. The LOD for ONOO⁻ is 42.12 nM, and the LOD for $Na_2S_2$ is 38.45 nM. In summary, the multi-signal fluorescent probe can realize the high-sensitivity discrimination and detection of ONOO⁻ and $Na_2S_2$.

It should be noted that described above are merely illustrative of the disclosure, and are not intended to limit the disclosure. Although the disclosure has been illustrated and described in detail above, it should be understood that those skilled in the art could still make modifications and replacements to the embodiments of the disclosure. Those modifications and replacements made by those skilled in the art based on the content disclosed herein without departing from the scope of the disclosure shall fall within the scope of the present disclosure defined by the appended claims.

In addition, the features of various embodiments may be combined in the absence of contradiction. The contents in the background are merely for better understanding of the general background of the application, and should not be considered as admitting or in any way implying that the content belongs to the prior art known to those skilled in the art.

What is claimed is:

1. A multi-signal fluorescent probe for early diagnosis of tumors, wherein a structural formula of the multi-signal fluorescent probe is shown as follows:

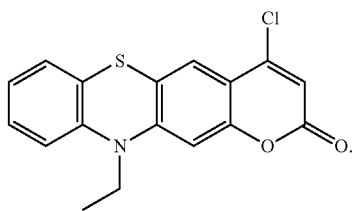 [SMILES: CCN1c2ccccc2Sc2cc3c(Cl)cc(=O)oc3cc21]

2. A method for preparing the multi-signal fluorescent probe of claim 1, comprising:
   adding 2-methoxyphenothiazine and ethyl iodide into a mixture of dichloromethane (DCM) and acetonitrile followed by a first reaction to obtain a reaction mixture; and subjecting the reaction mixture to a first post-treatment to obtain 10-ethyl-2-methoxy-10H-phenothiazine;
   adding boron tribromide into the 10-ethyl-2-methoxy-10H-phenothiazine under an inert gas followed by a second reaction under an ice bath and a second post-treatment to obtain 10-ethyl-10H-phenothiazin-2-ol; and
   mixing the 10-ethyl-10H-phenothiazin-2-ol, malonic acid, zinc chloride and phosphorus oxychloride followed by a third reaction and a third post-treatment to obtain the multi-signal fluorescent probe.

3. The method of claim 2, wherein the first reaction is performed at 65-75° C. for 8-12 h.

4. The method of claim 2, wherein the first post-treatment comprises:
   subjecting the reaction mixture to column chromatography to obtain the 10-ethyl-2-methoxy-10H-phenothiazine.

5. The method of claim 2, wherein the second reaction is performed under stirring in a dark environment for 4-6 h.

6. The method of claim 2, wherein the second post-treatment comprises:
   dropwise adding a red reaction solution resulted from the second reaction into ice water followed by pH adjustment to 6-7 and extraction with DCM to collect an organic layer; and
   concentrating the organic layer to obtain the 10-ethyl-10H-phenothiazin-2-ol.

7. The method of claim 2, wherein the third reaction is performed under reflux and stirring at 80-90° C. for 24-36 h.

8. The method of claim 2, wherein the third post-treatment comprises:
   dropwise adding a brown viscous solution resulted from the third reaction into ice water followed by pH adjustment to 6-7 and extraction with DCM to collect an organic layer; and
   subjecting the organic layer to concentration and column chromatography to obtain the multi-signal fluorescent probe.

9. The method of claim 6, wherein the pH adjustment is performed with a 20 wt. % sodium hydroxide aqueous solution.

10. The method of claim 8, wherein the pH adjustment is performed with a 20 wt. % sodium hydroxide aqueous solution.

* * * * *